United States Patent
Tellefsen et al.

(10) Patent No.: US 10,639,247 B2
(45) Date of Patent: May 5, 2020

(54) PIGMENT MIXTURES

(75) Inventors: Mark Tellefsen, Savannah, GA (US); Qinyun Peng, Moorestown, NJ (US)

(73) Assignee: Merck Patent Gesellschaft, Darmstadt (DE)

( * ) Notice: Subject to any disclaimer, the term of this patent is extended or adjusted under 35 U.S.C. 154(b) by 129 days.

(21) Appl. No.: 12/779,334

(22) Filed: May 13, 2010

(65) Prior Publication Data

US 2010/0291014 A1 Nov. 18, 2010

Related U.S. Application Data

(60) Provisional application No. 61/178,762, filed on May 15, 2009.

(51) Int. Cl.
*A61K 8/19* (2006.01)
*A61Q 1/02* (2006.01)
*A61K 8/02* (2006.01)
*A61K 8/26* (2006.01)
*A61K 8/36* (2006.01)
*A61K 8/25* (2006.01)
*A61Q 1/04* (2006.01)
*A61Q 1/10* (2006.01)
*A61Q 1/12* (2006.01)

(52) U.S. Cl.
CPC .............. *A61K 8/19* (2013.01); *A61K 8/0241* (2013.01); *A61K 8/0254* (2013.01); *A61K 8/25* (2013.01); *A61K 8/26* (2013.01); *A61K 8/361* (2013.01); *A61Q 1/02* (2013.01); *A61K 2800/412* (2013.01); *A61K 2800/43* (2013.01); *A61K 2800/59* (2013.01); *A61K 2800/612* (2013.01); *A61K 2800/651* (2013.01); *A61K 2800/872* (2013.01); *A61Q 1/04* (2013.01); *A61Q 1/10* (2013.01); *A61Q 1/12* (2013.01)

(58) Field of Classification Search
CPC ........ A61K 8/19; A61K 8/37; A61K 2800/43; A61K 8/0254; A61K 8/0241; A61K 8/361; A61Q 1/02; A61Q 1/04; A61Q 1/10
USPC .... 424/63, 653, 657, 69, 722; 106/401, 417, 106/418, 483, 489, 482, 486, 471, 419, 106/425, 436, 414, 453, 456, 493, 479
See application file for complete search history.

(56) References Cited

U.S. PATENT DOCUMENTS

| | | | |
|---|---|---|---|
| 3,647,492 A | | 3/1972 | Chapman et al. |
| 3,656,982 A | * | 4/1972 | Chapman et al. ............ 106/415 |
| 4,323,554 A | * | 4/1982 | Bernhard ........................ 424/63 |
| 4,390,524 A | * | 6/1983 | Nasuno et al. ................. 424/63 |
| 4,710,375 A | * | 12/1987 | Takasuka et al. .............. 424/69 |
| 4,863,800 A | | 9/1989 | Miyoshi et al. |
| 5,437,955 A | * | 8/1995 | Michlin .................... 430/108.4 |
| 5,885,342 A | * | 3/1999 | Gale et al. .................... 106/417 |
| 5,900,241 A | | 5/1999 | Roulier |
| 2003/0068285 A1 | | 4/2003 | Sandewicz et al. |
| 2004/0052743 A1 | | 3/2004 | Schmidt et al. |
| 2004/0120908 A1 | * | 6/2004 | Cohen et al. .................... 424/63 |
| 2008/0081028 A1 | * | 4/2008 | Tanaka ............................ 424/63 |
| 2010/0092527 A1 | | 4/2010 | Maeda et al. |
| 2010/0129465 A1 | * | 5/2010 | Blotsky .................. A61K 45/06 424/602 |

FOREIGN PATENT DOCUMENTS

| | | |
|---|---|---|
| CN | 1172426 A | 2/1998 |
| CN | 1185730 A | 6/1998 |
| EP | 0923927 A1 | 6/1999 |
| EP | 1329485 A1 | 7/2003 |
| JP | 2005187782 A | 7/2005 |
| JP | 2006298825 A | 11/2006 |
| JP | 2007045800 A | 2/2007 |
| JP | 2010077043 A | 4/2010 |
| WO | 1996021422 A1 | 7/1996 |
| WO | 2004045524 A2 | 6/2004 |
| WO | 2008133042 A1 | 11/2008 |

OTHER PUBLICATIONS

Encyclopedia Britannica, Alkaline-earth metal, [Retrieved from internet <URL: http://www.britannica.com/science/alkaline-earth-metal >], [Downloaded Jun. 25, 2015], 1 page.*
Schlanz et al. (Mica, Industrial Minerals and Rocks—Commodities, Markets, and Uses (7th ed., Kogel et al., editor) (Society for Mining, Metallurgy, and Exploration, 2006), Chapter 49 (available from Knovel), pp. 637-652).*
Citation information for Schlanz et al (4 pages).*
Official Action from corresponding Japanese Patent Application No. 2010-111758, dated Jun. 26, 2014, and English Translation thereof.
Official Action related to corresponding Chinese Patent Application No. 201010239651.8, dated Jun. 16, 2014.
English European Search Report in related application No. EP 10004632—date of completion Jun. 24, 2015.
English Abstract of EP 0923927—publication date Jun. 23, 1999.
English Abstract of JP 2006298825—publication date Jul. 23, 2003.
Official Action related to corresponding Chinese Patent Application No. 201610107866.1, dated Jun. 19, 2017.

* cited by examiner

*Primary Examiner* — Mark V Stevens
(74) *Attorney, Agent, or Firm* — Millen, White, Zelano & Branigan, PC; Ryan Pool

(57) ABSTRACT

Disclosed are pigment mixtures containing at least two components, where component A contains bismuth oxychloride (BiOCl) or boron nitride (BN) and component B contains synthetic flakes treated with at least one metal soap or mineral flakes treated with at least one metal soap and to the use thereof especially in cosmetic formulations.

18 Claims, No Drawings

PIGMENT MIXTURES

This application claims the benefit of the filing date of U.S. Provisional Application Ser. No. 61/178,762 filed May 15, 2009, which is incorporated by reference herein.

The present invention relates to pigment mixtures containing at least two components, where component A comprises bismuth oxychloride (BiOCl) or boron nitride (BN) and component B comprises synthetic flakes treated with at least one metal soap or mineral flakes treated with at least one metal soap and to the use thereof especially in cosmetic formulations.

The performance features of bismuth oxychloride are well known. BiOCl powders and pearlescent pigments are for example disclosed in German Patent 10 03 377, U.S. Pat. No. 2,975,053, DE 24 11 966, EP 0 496 686 B1 and DE 43 05 280 A1. Bismuth oxychloride by virtue of the flake structure of the particles, which is a fractal extension of the laminar crystal structure, has highly desirable intrinsic properties, such as a very soft and slippery skin feel akin to the lubricity of a fluid, hydrophobicity (repulsion to water) and/or oleophylicity (affinity to oil), a high adhesiveness to the skin, as well as a compactibility and binding action to hold particles in compressed form without the need for a fluid binder. It is a white or off-white powder, depending on the particle size. It can also provide a satiny luster by virtue of the enhanced specular reflection from smooth flakes of high refractive index. Bismuth oxychloride is often combined with other ingredients because of these tactile and visual properties.

Boron nitride is also well known. It has a graphite-like structure and provides excellent lubricity in dry powder, similar to bismuth oxychloride. Boron nitride has advantages due to the low refractive index and the low density. The hiding powder is relatively low and this means that when combined with colorants, the color intensity comes through. Furthermore, the payout in terms of the improvement in skin feel is very good, i.e. the specific surface area is relatively high. However, boron nitride doesn't provide very much luster, especially for fine particle sizes, due to the low refractive index and light scattering from smaller flakes. Conversely, coarse particle size boron nitride flakes, although they appear more lustrous and sparkly as a neat (unextended) material, they also feel coarse and gritty on the skin.

The use of metal soaps (alkaline earth salts of fatty acids) as treatments to render improved tactile properties of cosmetic powders, especially of flake or platy shape particles, is well known, for example from the product literature such as Brenntag, Cardre, Kobo, Miyoshi/US Cosmetics, etc. Metal soaps are also well known as a commercially available ingredient which can be added as a pure solid into cosmetic formulations. It provides a similar softness, hydrophobicity and fluidity as compared to waxes, but the performance is yet distinctive in performance. As such, the benefit of enhanced skin feel imparted by blended magnesium stearate is limited by the lack of intimate comingling of metal soap due to the relatively large particle size of the powder.

Furthermore, the use of aqueous deposited metal soaps as a binder for enhanced inter-particle adhesion is known from U.S. Pat. Nos. 4,863,800, 3,647,492, 3,656,982. Bismuth oxychloride, iron oxides and mica have been claimed to have been bound together by precipitated metal soap. The state of the art includes the limited skin feel enhancement of treatment of metal soap for powders of non-flaky particle shape, such as pigmentary iron oxides, zinc oxide or titanium dioxide.

In Cosmetics & Toiletries, Vol. 115, August 2000, pages 45-51, is disclosed that an enhanced reduction of friction is rendered by magnesium myristate treatment of sericite.

The suitability of wet ground mica for its benefits in cosmetic applications such as skin feel has been disclosed. Conversely, "Evaluation of Feel: Lauroyl Lysine Treated Pigments" published in Cosmetics and Toiletries pages 85-90, (1992) states that fine mica with average size of 8.5 µm or finer is inferior in skin feel as compared to larger flake sizes.

The object of the present invention was to provide a pigment mixture containing BiOCl or BN powder with enhanced skin feel which can be incorporated well into the respective application system and is stable therein. Furthermore, the slippery smooth and soft skin feel as a cosmetic ingredient are improved in comparison with existing products on the market. Other advantages include improved payout and compressibility, especially on a per weight basis.

Surprisingly, it is found that there is a synergy when a metal soap, for example magnesium stearate, treated natural or synthetic powder in flake form, for example mica flakes, is mixed with bismuth oxychloride or boron nitride, due to interleafing of the two types of flake particles. The skin feel of the mixture is as good as or better than either ingredient alone. In addition, the luster surprisingly does not decrease as the higher refractive index BiOCl is replaced by lower refractive index mica. That is, the lower the bismuth oxychloride level, the less lustrous the mixture should be. On the contrary, the luster increases with the decreased amount of bismuth oxychloride.

The invention thus relates to a pigment mixture containing at least two components, where component A comprises bismuth oxychloride (BiOCl) or boron nitride (BN) and component B comprises synthetic flakes treated with at least one metal soap or mineral flakes treated with at least one metal soap.

Component A are preferably BiOCl pigments. The admixing of component B, preferably with a metal soap treated mica flakes, with component A, preferably, BiOCl pigments, enables increased lustre to be imparted to the application systems and shows an increased skin feeling in cosmetics compared to BiOCl alone. At the same time, the mixture is distinguished by its variable, i.e. controllable, hiding power from virtually invisible to strongly hiding. In addition, the functionality of the end product is improved. Formulations comprising the mixture according to the invention have an excellent skin feel, high skin affinity, long-wear properties, variable hiding power, if desired, lustre, ease of incorporation into the end product, and comparatively high light stability.

The composition of small amounts of at least one metal soap, for example magnesium stearate (for example 2 wt. % per wet ground mica powder 98 wt. %), if combined as an intimate aqueous deposition of stearate onto the mica surface and subsequently blended with 10-90% bismuth oxychloride powder, has an unexpectedly good skin feel (slip aka. lubricity and cushion aka. compressive yield) which matches or exceeds that of the pure bismuth oxychloride powder.

Subsequently, the skin feel of these of pigment mixtures showed the improved properties above than the individual components surprisingly independent of the ratios of the mixture.

The novelty of natural or synthetic flakes, for example mica flakes, treated with at least one metal soap, for example magnesium stearate, stems from combination of two factors:
[1] the intimate comingling of fine magnesium stearate particles as described above
and
[2] the thinness, smoothness and particle size distribution of the mica flakes.

A key feature is the combination of intimately deposited magnesium stearate characterized by a softness and non-polarity with the mica flakes characterized by rigidity (i.e. shape retaining) but yet flexibility (yielding to torsional stress). It is preferred to employ wet ground mica derived from suitable mineral deposits such as pegmatite mica. Schist or sericite type fine mica is much less desirable. Dry ground mica is less suitable. Alternatively, suitable preparation of synthetic mica, e.g. fluorophlogopite, including careful growth of the books of mica and subsequent wet grinding, can also be quite suitable. The mica flakes should be characterized by a high aspect ratio, i.e. high thinness compared to lateral breadth or diameter. The flakes should be relatively free from steps on the surfaces and fraying at the edges. The fraction of the mica flakes should be refined by removal of fine mica flakes typically by elutriation until they are sufficiently depleted. It is also important and thus preferred to remove any other fine mechanical impurities as well. See Kirk Othmer Encyclopedia of Chemical Technology $4^{th}$ Edition, Vol 16, p. 556 (1991) for a description of wet ground mica.

There are several distinguishing features of the treated mica in this invention. The nature of the mica flake is an important aspect and there is a lack of a need for surfactant or triglyceride ester version rather than simply the salt of the fatty acid. The preferred composition requires no surfactant. Magnesium stearate treated mica, preferably on mica of wet ground quality and of fine particle size preferably 2-20 µm and even better 2-10 µm has a skin feel which is as good as the best feeling grade of bismuth oxychloride. Although Miyoshi, Kobo, Cardre and Brenntag BSI all already offer mica treated with so-called metal soaps, e.g. magnesium myristate, we have yet to find a rival to the skin feel provided by the embodiment of this invention.

The invention likewise relates to the use of the mixture according to the invention in cosmetic formulations.

The variation of the ratio of each ingredient A and B can offer a wide selection of choices in terms of luster and opacity. In addition, it is possible to make much more lustrous powder than either bismuth oxychloride or BN (=component A) or natural or synthetic flakes, for example mica, alone.

The ratio of component A to component B is preferably from 10:90 to 90:10 and particularly preferable from 30:70 to 70:30. In a preferred embodiment, the ratio of BiOCl (component A) to treated mica flakes (component B) is preferably from 10:90 to 90:10 and particularly preferable from 30:70 to 70:30.

Powder BiOCl products are commercially available and are offered, for example, by Merck KGaA, Germany, and Rona, EMD Chemicals, under the trade names Biron®, Bital®, Mibiron® and Ronaflair™ and by BASE under the trade names Pearl Glo, Bi-Lite, Mearlite.

Owing to the diverse production possibilities, BiOCl powders having different optical properties, from matt to glossy and from transparent to hiding, are obtainable. The size of the individual BiOCl pigment particles is 1-100 µm, preferably 1-40 µm and in particular 2-35 µm. The particles can also be in small agglomerates which can be up to 100 µm but preferably no greater than 75 µm. The BiOCl powders can optionally be treated with metal soaps or with other treatments such as silicones or other hydrophobic substances.

Component B are preferably synthetic flakes selected from the group of mica, silica, alumina, borosilicates, aluminosilicate or mineral flakes selected from mica, clay, talc and/or kaolin. Especially preferred, component B comprises natural or synthetic mica flakes treated with a metal soap.

Preferred mixtures comprise mica treated with alkaline earth metal stearate such as magnesium stearate, zinc stearate, aluminum stearate, or calcium stearate. Other deprotonated fatty acid anion components besides stearate could include isostearate (branched or non-linear), hydrogenated ricinoleate (a.k.a. hydroxystearate), arachidate, palmitate, oleate, myristate, laurate, caprate or caprylate.

Preferred stearates of the alkaline earth metal stearates are selected from magnesium stearate, calcium stearate, barium stearate, zinc stearate and aluminium stearate. Especially preferred are mica flakes treated with magnesium stearate or zinc stearate.

The pigment mixture according to the present invention is prepared in the way that component A and component B and optionally further constituents are blended.

The preferred method of treatment is to deposit by aqueous precipitation the metal soap to give an intimate mixture with the natural or synthetic flakes, for example mica flakes, as a suspension in water. The treated suspension is then dewatered and dried. The precipitation occurs by adding multivalent salt in solution to the hot water solution of the sodium salt of the soap. The sodium salt of the soap can also be generated in situ beforehand by neutralization of a dispersion of the fatty acid with sodium hydroxide. Another non-critical option is to precipitate the metal soap to suspensions of the natural or synthetic flakes, for example mica flakes, with component A, for example BiOCl, and optionally to other insoluble components.

The amount of the metal soap, preferably stearate including isostearate or a mixture of stearates on the surface of the mineral or synthetic flakes, preferably mica flakes, is 0.1-10 wt. %, preferably 0.5-5 wt. %, especially preferred 1-3 wt. % based on the total weight of mineral or synthetic flakes.

Particularly preferred mixtures comprise BiOCl+mica coated with magnesium stearate including the following representative compositions:
- 68.6% synthetic or natural mica+1.4% magnesium stearate+30% BiOCl
- 68.6% synthetic or natural mica+1.4% magnesium stearate+15% BiOCl+15% zinc oxide
- 68.6% synthetic or natural mica+1.4% magnesium stearate+25% BiOCl+5% zinc oxide
- 49% synthetic or natural mica+1% magnesium stearate+50% BiOCl
- 49% synthetic or natural mica+1% magnesium stearate+45% BiOCl+5% zinc oxide.

Suitable flakes of component B generally have a thickness of 0.2-2 µm, in particular 0.3-1.0 µm. The extension in the two other dimensions is usually 1-100 µm, preferably 2-50 µm, and in particular 2-20 µm.

Particularly suitable are platelet-shaped mica substrates which are of synthetic or natural origin. Especially preferred are mica substrates which are wet ground flakes. Suitable mica flakes generally have a thickness of 0.2-2 µm, in particular 0.3-1.0 µm. The extension in the two other dimensions is usually 1-100 µm, preferably 2-50 µm, and in particular 2-20 µm.

Wet grinding is achieved by submitting heavy pastes of coarse mica flakes to milling under high shear and low impact. Unlike dry milling which produces flakes of highly distorted shape, the output of wet grinding gives a thin, uniform flake of extremely high surface area, but also highly uniform shape (uniform in thickness and smooth, with minimal step deformities and edge fraying). The very thin, but yet smooth, uniform and regular wet-ground mica flakes are preferred for use in cosmetics wherein superior tactile performance (skin feel, slip or lubricity and soft cushion) is critical.

The pigment mixtures are also versatile and can accommodate other ingredients, such as treated or untreated zinc oxide, titanium dioxide, iron oxides and silica as well as organic or inorganic colorants of natural and synthetic origin. Preferred colorants include carmine, iron blue or chromium oxide greens, ultramarines, manganese violet, FD&C and D&C colorants. These additives have minimum effect on the tactile properties of the mixture, even though such additives are not flakes. The skin feel of this type of mixture is quite accommodating.

The mixture according to the invention is simple and easy to handle. The mixture can be incorporated into the application system by simple stirring-in in the form of a powder. Complex grinding and dispersion of the mixtures is unnecessary and in some cases counter-productive.

The concentration of the mixture in the application system, preferably in cosmetic formulations, is generally up to 70% by weight, preferably up to 50% by weight. It is generally dependent on the specific application.

The pigment mixtures according to the invention are advantageously employed in color/decorative and personal care cosmetics. Mixtures according to the invention comprising BiOCl or BN in the form of a powder are used, in particular, in eye shadow, rouge, cosmetic sticks, pencils and make-up powders of all types. The cosmetic products are distinguished by particularly interesting tactile and/or color effects. In color cosmetics, the mixtures according to the invention enable particularly uniform application of the powder to the skin and result in an improvement in the skin feel. In addition, the skin adhesion is improved and enhances binding of pressed powders. Furthermore, the mixture according to the invention in the cosmetic formulation exhibits an improvement in slip and cushion as well as ease of application and distribution, and variable hiding power from transparent to hiding and/or from matt to glossy lustre.

The pigment mixture can furthermore be mixed with commercially available state-of-the-art fillers. Fillers which may be mentioned are, for example, uncoated natural and synthetic mica, glass beads or glass powder, nylon powder, polymethylmethacrylate powders, pure or filled melamine resins, talc, glasses, kaolin, oxides or hydroxides of aluminium, magnesium, calcium or zinc, BiOCl, barium sulfate, calcium sulfate, calcium carbonate, magnesium carbonate, carbon, boron nitride and physical or chemical combinations of these substances. There are no restrictions regarding the particle shape of the filler. In accordance with requirements, it can be, for example, flake-form, spherical, needle-shaped, crystalline or amorphous.

The pigment mixture according to the invention can of course also be combined in the formulations with cosmetic raw materials and auxiliaries of any type. These include, inter alia, oils, fats, waxes, film formers, surfactants, antioxidants, such as, for example, vitamin C or vitamin E, stabilisers, odour intensifiers, silicone oils, emulsifiers, solvents, such as, for example, ethanol, or ethyl acetate or butyl acetate, preservatives and auxiliaries which generally determine applicational properties, such as, for example, thickeners and rheological additives, such as, for example, bentonites, hectorites, silicon dioxides, Ca silicates, gelatines, high-molecular-weight carbohydrates and/or surface-active auxiliaries, etc.

The formulations comprising the pigment mixtures according to the invention can belong to the lipophilic, hydrophilic or hydrophobic type. In the case of heterogeneous formulations having discrete aqueous and non-aqueous phases, the pigment mixtures according to the invention may in each case be present in only one of the two phases or alternatively distributed over both phases.

The pH of the cosmetic formulations can be between 1 and 14, preferably between 2 and 11 and particularly preferably between 5 and 8. The pigment mixture according to the invention may furthermore also be combined with cosmetic active ingredients. Suitable active ingredients are, for example, insect repellents, inorganic UV filters, such as, for example, $TiO_2$, UV A/BC protective filters (for example OMC, B3 and MBC), also in encapsulated form, anti-ageing active ingredients, vitamins and derivatives thereof (for example vitamin A, C, E, etc.), self-tanning agents (for example DHA, erythrulose, inter alia), and further cosmetic active ingredients, such as, for example, bisabolol, LPO, VTA, ectoine, emblica, allantoin, bioflavonoids and derivatives thereof.

Organic UV filters are generally incorporated into cosmetic formulations in an amount of 0.5 to 10% by weight, preferably 1 to 8%, and inorganic filters in an amount of 0.1 to 30%.

The pigment mixture according to the invention may in addition comprise further conventional skin-protecting or skin-care active ingredients. These may in principle be any active ingredients known to the person skilled in the art. Particularly preferred active ingredients are pyrimidine carboxylic acids and/or aryl oximes.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic preparations, such as powders, soaps, surfactant-containing cleansing products, lipsticks, rouge, make-up, care creams and sunscreen compositions.

Application forms of the cosmetic formulations which may be mentioned are, for example: solutions, suspensions, emulsions, PIT emulsions, pastes, ointments, gels, creams, lotions, powders, soaps, surfactant-containing cleansing compositions, oils, aerosols and sprays. Examples of other application forms are sticks, shampoos and shower preparations. Any desired customary excipients, auxiliaries and, if desired, further active ingredients may be added to the preparation.

Ointments, pastes, creams and gels may comprise the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary excipients, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary excipients, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary excipients, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary excipients, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary excipients, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary excipients, such as synthetic oils, such as, for example, fatty acid esters, fatty alcohols, silicone oils, natural oils, such as vegetable oils and oily plant extracts, paraffin oils, lanolin oils, or mixtures of these substances.

The cosmetic preparations may exist in various forms. Thus, they can be, for example, a solution, a water-free preparation, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable.

Preference is given to emulsions. O/W emulsions are particularly preferred. Emulsions, W/O emulsions and O/W emulsions are obtainable in a conventional manner.

Further embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

Solid sticks consist of natural or synthetic waxes and oils, fatty alcohols, fatty acids, fatty acid esters, lanolin and other fatty substances.

If a preparation is formulated as an aerosol, the customary propellants, such as alkanes, fluoroalkanes and chlorofluoroalkanes, are generally used.

Cosmetic formulations having light-protection properties may comprise adjuvants, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used in the cosmetic field.

The invention thus furthermore also relates to formulations comprising the pigment mixture according to the invention in combination with at least one constituent selected from the group of absorbents, astringents, antimicrobial substances, antioxidants, antiperspirants, antifoaming agents, antidandruff active ingredients, antistatics, binders, biological additives, bleaching agents, chelating agents, deodorants, emollients, emulsifiers, emulsion stabilisers, dyes, humectants, film formers, fillers, odour substances, flavour substances, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

In addition, the pigment mixture according to the invention can be used in films and plastics, gift foils, plastic containers and mouldings for all applications known to the person skilled in the art. Suitable plastics for the incorporation of the filler pigments according to the invention are all common plastics, for example thermosets or thermoplastics. The description of the possible applications and the plastics which can be employed, processing methods and additives are given, for example, in RD 472005 or in R. Glausch, M. Kieser, R. Maisch, G. Pfaff, J. Weitzel, Perlglanzpigmente [Pearlescent Pigments], Curt R. Vincentz Verlag, 1996, 83 ft, the disclosure content of which is also incorporated herein.

The pigment mixtures according to the invention are likewise suitable in the above-mentioned areas of application for use in blends with organic dyes and/or pigments, such as, for example, transparent and opaque white, coloured and black pigments, and with flake-form iron oxides, BiOCl, organic pigments, holographic pigments, LCPs (liquid crystal polymers) and conventional transparent, coloured and black lustre pigments based on metal oxide-coated flakes based on mica, glass, $Al_2O_3$, $Fe_2O_3$, $SiO_2$, metal flakes, etc. The filler pigments according to the invention can be mixed in any ratio with commercially available pigments and fillers.

The pigment mixtures according to the invention are furthermore suitable for the preparation of flowable pigment compositions and dry preparations comprising the pigment mixture, binders and optionally one or more additives. Dry preparations is also taken to mean preparations which comprise from 0 to 8% by weight, preferably from 2 to 8% by weight, in particular from 3 to 6% by weight, of water and/or a solvent or solvent mixture. The dry preparations are preferably in the form of pellets, granules, chips, sausages or briquettes and have particle sizes of 0.2-80 mm. The dry preparations are used, in particular, in the preparation of printing inks and in cosmetic formulations.

Without further elaboration, it is believed that one skilled in the art can, using the preceding description, utilize the present invention to its fullest extent.

The invention thus also relates to formulations comprising the mixture according to the invention.

The following preferred specific embodiments are, therefore, to be construed as merely illustrative, and not limitative of the remainder of the disclosure in any way whatsoever.

The following examples below are intended to illustrate the invention, but without restricting it. Percentages are by weight, unless otherwise noted. In the examples, all temperatures are set forth unconnected in degrees Celsius; unless otherwise indicated, all parts and percentages are by weight.

EXAMPLES

Example 1: Treatment of Natural Mica

Wet ground natural muscovite mica of particle size 2-19 µm of quantity 200 g is suspended at approximately 10% by stirring in deionized water at 65° C. Sodium stearate (Brenntag) of 4.0 g quantity, enough to form 2% magnesium stearate is delivered and dissolved. Subsequently 1.3 g magnesium chloride (hexahydrate) is delivered. The suspension of precipitated magnesium stearate can be elutriated with deionized water to remove sodium chloride salts by sedimentation and or filtration and then the wet mixture is dried and the product is ready for blending.

The treated natural mica exhibits a very good skin feel.

Example 2: Treatment of Synthetic Mica

The method employed in example 1 is repeated except in place of natural mica, synthetic mica of particle size 5-25 µm is employed.

The treated synthetic mica exhibits a very good skin feel.

Example 3: Mixture of 49% Synthetic Mica/50% BiOCl/1% Magnesium Stearate

A mica treated as per Example 2 is blended at equal weight with a cosmetic grade BiOCl in a laboratory blender (Waring or Oster).

Example 4: Mixture of 68.6% Synthetic Mica/15% BiOCl/15% ZnO/1.4% Magnesium Stearate A mica treated as per Example 2 is blended at 70% per total weight along with 15% of a cosmetic grade BiOCl and 15% of a cosmetic grade zinc oxide in a laboratory blender (Waring or Oster).

USE EXAMPLES

Use Example 1: Loose Powder Eye Shadow

| Phase | Ingredient | Composition | Manufacturer | % |
|---|---|---|---|---|
| A | BiOCl/mica mixture according to Example 3 | | | 40.00 |
| | Colorona ® Copper Fine | Mica, iron oxide | (1) | 30.00 |
| | Supra H | Talc | (2) | 16.90 |
| | Zea Mays (Corn) Starch | Corn Starch | (3) | 7.00 |
| | Propylparaben | Propylparaben | (4) | 0.10 |
| B | Pelemol OP | Octyl Palmitate | (5) | 6.00 |

Preparation:

Mix the ingredients of Phase A homogeneously. Add Phase B with stirring.

Sources of Supply:
(1) Merck KGaA
(2) Luzenac
(3) Argo Brand Corn Starch/Corn Products
(4) Spectrum Chemical
(5) Phoenix Chemical

Use Example 2: Mineral Make-Up

| Phase | Ingredient | Composition | Manufacturer | % |
|---|---|---|---|---|
| A | BiOCl/mica mixture according to Example 3 | | | 48.00 |
| | SunChroma Brown | Iron oxides | (1) | 12.00 |
| | RonaFlair ™ Low Luster | Mica, barium sulfate and titanium dioxide | (2) | 22.00 |
| | RonaFlair ™ MTU | Bismuth oxychloride | (2) | 10.00 |
| | RonaFlair ™ LDP | Silica, titanium dioxide and iron oxides | (2) | 5.00 |
| | Colorona ® Oriental Beige | Mica, titanium dioxide and iron oxides | (2) | 3.00 |

Preparation:

Mix the ingredients of Phase A homogeneously.

Sources of Supply:
(1) Sun Chemical
(2) Merck KGaA

Example 3: Eye Pencil

| Phase | Ingredient | Composition | Manufacturer | % |
|---|---|---|---|---|
| A | Supra H | Talc | (1) | 11.30 |
| | Syncrowax ERL-C | C18-36 Ethylene Glycol Ester | (2) | 8.10 |
| | Syncrowax HR-C | Glyceryl Tribehenate | (2) | 1.90 |
| | Pelemol OP | Ethyl Hexyl Palmitate | (3) | 38.40 |
| | Myritol 318 | Caprylic/Capric Triglyceride | (4) | 4.00 |
| | Emersol 120 | Stearic Acid | (4) | 3.00 |
| | Emerest 2452 | Polyglyceryl 3-Diisostearate | (4) | 0.50 |
| | Methylparaben | Methylparaben | (5) | 0.20 |
| | Propylparaben | Propylparaben | (5) | 0.10 |
| B | BiOCl/mica mixture according to Example 3 | | | 15.00 |
| | Colorona ® Bordeaux | Iron oxide, mica | (6) | 16.00 |
| | Colorona ® Mica Black | Iron oxide, mica | (6) | 1.50 |

Preparation:

Combine all ingredients in Phase A and heat to 80-85° C. with stirring until homogenous. Add Phase B ingredients. Agitate with a high-speed mixer until no agglomerates remain. Pour at 70° C.

Sources of Supply:
(1) Luzenac
(2) Croda
(3) Phoenix Chemical
(4) Cognis
(5) Spectrum Chemical
(6) Merck KGaA

Example 4: Pressed Eye Shadow

| Phase | Ingredient | Composition | Manufacturer | % |
|---|---|---|---|---|
| A | Supra H | Talc | (1) | 35.50 |
|  | Dry Flo PC | Aluminum Starch Octenyl Succinate | (2) | 7.00 |
|  | Magnesium Stearate Vegetable F.G. | Magnesium Stearate | (3) | 2.00 |
| B | BiOCl/mica mixture according to Example 3 |  |  | 15.00 |
|  | Colorona ® Majestic Green | Titanium dioxide, mica, and chromium oxide greens | (4) | 22.00 |
|  | Colorona ® Dark Blue | Titanium dioxide, mica and ferric ferrocyanide | (4) | 8.00 |
| C | Lexol 3975 | Isopropyl palmitate, isopropyl myristate and isopropyl stearate | (5) | 9.20 |
|  | Cutina CP | Cetyl palmitate | (6) | 0.60 |
|  | Snow White Petrolatum | Petrolatum | (7) | 0.60 |
|  | Propylparaben | Propylparaben | (8) | 0.10 |

Preparation:

Combine ingredients in Phase A. Pulverize with a hammer mill, passing twice through a 0.027" herring bone screen. Add Phase B with gentle agitation. Combine Phase C with mixing; heat to 70° C. Spray Phase C onto batch while agitating bulk. Pass entire batch through a jump gap. Mix gently and press into disks.

Sources of Supply:

(1) Luzenac
(2) National Starch & Chemical
(3) Brenntag BSI
(4) Merck KGaA
(5) Inolex
(6) Cognis
(7) Penreco
(8) Spectrum Chemical

Example 5: Creamy Eye Shadow

| Phase | Ingredient | Composition | Manufacturer | % |
|---|---|---|---|---|
| A | Colorona ® Dark Blue | TiO₂, mica, iron blue | (1) | 10.00 |
|  | Timiron ® Supersheen MP-1001 | TiO₂, mica | (1) | 10.00 |
|  | BiOCl/mica mixture according to Example 3 |  | (1) | 10.00 |
|  | Talcum | Talc | (1) | 10.00 |
| B | Crodamol PMP | PEG-2 Myristyl Ether Propionate | (2) | 32.90 |
|  | Syncrowax HGLC | C18-36 Acid Triglyceride | (2) | 10.00 |
|  | Syncrowax HRC | Tribehenin | (2) | 3.00 |
|  | Miglyol 812 neutral oil | Caprylic/Capric Triglyceride | (3) | 9.00 |
|  | Stearic acid | Stearic Acid | (1) | 3.00 |
|  | Antaron V-216 | PVP/Hexadecene Copolymer | (4) | 2.00 |
|  | Oxynex ® K liquid | Tocopherol, Ascorbyl Palmitate, Ascorbic Acid, Citric Acid, PEG-8 | (1) | 0.10 |
|  | Preservative | Propylparaben |  | q.s. |

Preparation:

Heat phase B at about 80° C. until everything has melted, and cool to 65° C. The constituents of phase A are then added with stirring, and the finished eye shadow is packed while still liquid.

Sources of Supply:

(1) Merck KGaA
(2) Croda
(3) Hüls AG
(4) ISP Europe

Example 6: Lip Powder

| Phase | Ingredient | Composition | Manufacturer | % |
|---|---|---|---|---|
| A | Colorona ® Bordeaux | Iron oxide, mica | (1) | 30.00 |
|  | BiOCl/mica mixture according to Example 4 |  | (1) | 25.00 |
|  | Talcum | Talc | (1) | 30.00 |
| B | Isopropyl stearate | Isopropyl Stearate | (2) | 11.20 |
|  | Dow Corning 1403 fluid | Dimethicone, Dimethiconol | (3) | 3.80 |
|  | Perfume oil |  |  | q.s. |
|  | Preservative | Propylparaben |  | q.s. |

Preparation:

Combine and pre-mix the constituents of phase A. Subsequently add the molten phase B dropwise to the powder mixture with stirring. The powders are pressed at 40-50 bar.

Sources of Supply:

(1) Merck KGaA
(2) Henkel KGaA
(3) Dow Corning

Without further elaboration; it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and U.S. Provisional Application Ser. No. 61/178,762, filed May 5, 2009, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A pigment mixture comprising at least two components, where component A comprises:
   i) optionally coated bismuth oxychloride (BiOCl) or optionally coated boron nitride (BN) in the particle size range of 1-40 µm and component B comprises:
   ii) synthetic flakes or mineral flakes in the particle size range of 1-100 µm, wherein a metal soap has been intimately deposited onto the surface of said synthetic flakes or mineral flakes, wherein said metal soap is an alkaline earth metal stearate or branched or non-linear isostearate, zinc stearate, aluminum stearate or a mixture thereof, and wherein component B excludes optionally coated bismuth oxychloride (BiOCl) and optionally coated boron nitride (BN) and, wherein i) and ii) have been blended in a ratio of 10:90 to 90:10 by weight and form an intimate comingling, and wherein the amount of metal soap on the surface of the mineral or synthetic flakes is 0.1-10 wt. % based on the total weight of mineral or synthetic flakes.

2. A pigment mixture according to claim 1, wherein component A is bismuth oxychloride (BiOCl).

3. A pigment mixture according to claim 1, wherein component B comprises synthetic flakes which are mica, silica, alumina, borosilicate, and/or aluminosilicate.

4. A pigment mixture according to claim 1, wherein component B comprises mineral flakes which are of mica, clay, talc and/or kaolin.

5. A pigment mixture according to claim 1, wherein component B comprises natural or synthetic mica flakes treated with a metal soap wherein said metal soap is an alkaline earth metal stearate or branched or non-linear isostearate, zinc stearate, aluminum stearate or a mixture thereof.

6. A pigment mixture according to claim 1, wherein the synthetic or mineral flakes are wet ground natural muscovite mica with particle size 2-19 µm, or synthetic mica with particle size 5-25 µm.

7. A pigment mixture according to claim 1, wherein the metal soap is an alkaline earth metal branched or non-linear isostearate.

8. A pigment mixture according to claim 1, wherein metal soap is an alkaline earth metal stearate which is magnesium stearate, barium stearate, or calcium stearate or a mixture thereof.

9. A pigment mixture according to claim 1, wherein component B comprises natural or synthetic mica flakes treated with magnesium stearate or zinc stearate.

10. A pigment mixture according to claim 1, wherein i) and ii) are mixed in a ratio of 30:70 to 70:30 by weight.

11. A pigment mixture according to claim 1, further comprising another powder, a cosmetic grade of zinc oxide, titanium dioxide, iron oxide, ultramarine pigments, manganese violet, carmine, chromium oxide green, iron blue or organic pigments, a FD&C or D&C colorant.

12. A pigment mixture according to claim 1, comprising by weight %
   68.6% synthetic or natural mica and 1.4% magnesium stearate as component B, and 30% BiOCl as component A;
   or
   68.6% synthetic or natural mica and 1.4% magnesium stearate as component B, and 15% BiOCl as component A, and 15% zinc oxide;
   or
   68.6% synthetic or natural mica and 1.4% magnesium stearate as component B, and 25% BiOCl as component A, and 5% zinc oxide;
   or
   49% synthetic or natural mica and 1% magnesium stearate as component B, and 50% BiOCl as component A;
   or
   49% synthetic or natural mica and 1% magnesium stearate as component B, and 45% BiOCl as component A, and 5% zinc oxide.

13. A pigment mixture according to claim 1, further comprising at least one constituent selected from the group consisting of absorbents, astringents, antimicrobial substances, antioxidants, antiperspirants, antifoaming agents, antidandruff active ingredients, antistatics, binders, biological additives, bleaching agents, chelating agents, deodorants, emollients, emulsifiers, emulsion stabilisers, dyes, humectants, film formers, fillers, odour substances, flavour substances, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

14. A process for preparing a pigment mixture according to claim 1, comprising blending component A and component B and optionally further constituents, or mixing component A and mineral or synthetic flakes and the metal soap and optionally further constituents as a suspension in water and then dewatering and drying the suspension.

15. A cosmetic composition comprising a pigment mixture according to claim 1 and a cosmetically acceptable carrier.

16. A pigment mixture comprising at least two components, where component A comprises:
   i) optionally coated bismuth oxychloride (BiOCl) or optionally coated boron nitride (BN) and
   component B comprises:
   ii) synthetic flakes or mineral flakes in the particle size range of 1-100 µm, wherein a metal soap has been intimately deposited onto the surface of said synthetic flakes or mineral flakes, which metal soap is an alkaline earth metal stearate or branched or non-linear isostearate, zinc stearate, aluminum stearate or a mixture thereof,
   wherein i) and ii) are mixed in a ratio of 10:90 to 90:10 by weight, and wherein said synthetic flakes or mineral flakes are wet ground mica, and
   wherein the amount of metal soap on the surface of the mineral or synthetic flakes is 0.1-10 wt. % based on the total weight of mineral or synthetic flakes.

17. A pigment mixture according to claim 1, which contains uncoated bismuth oxychloride (BiOCl) or uncoated boron nitride (BN).

18. A pigment mixture consisting of two components, where
   component A consists of bismuth oxychloride (BiOCl) or boron nitride (BN) and component B consists of synthetic flakes or mineral flakes in the particle size range of 1-100 μm, wherein a metal soap has been intimately deposited onto the surface of said synthetic flakes or mineral flakes, which metal soap is an alkaline earth metal stearate or branched or non-linear isostearate, zinc stearate, aluminum stearate or a mixture thereof, wherein component A and component B are mixed in a ratio of 10:90 to 90:10 by weight, and wherein the amount of metal soap on the surface of the mineral or synthetic flakes is 0.1-10 wt. % based on the total weight of mineral or synthetic flakes.

* * * * *